United States Patent [19]

Wilsch-Irrgang et al.

[11] Patent Number: 5,750,490
[45] Date of Patent: May 12, 1998

[54] DETERGENT MIXTURES

[75] Inventors: Anneliese Wilsch-Irrgang, Sprockhoevel; Fred Schambil, Monheim; Theodor Voelkel, Erkrath, all of Germany; Miguel Osset, Barcelona; Rafael Pi, Granollers, both of Spain

[73] Assignee: Henkel Kommanditgesellschaft auf Aktien, Duesseldorf, Germany

[21] Appl. No.: 687,587

[22] PCT Filed: Jan. 23, 1995

[86] PCT No.: PCT/EP95/00230

§ 371 Date: Jul. 31, 1996

§ 102(e) Date: Jul. 31, 1996

[87] PCT Pub. No.: WO95/20640

PCT Pub. Date: Aug. 3, 1995

[30] Foreign Application Priority Data

Jan. 31, 1994 [DE] Germany .......................... 44 02 852.0

[51] Int. Cl.$^6$ ..................................................... C11D 1/62
[52] U.S. Cl. .......................... 510/504; 510/125; 510/299; 510/329; 510/492
[58] Field of Search ............................. 510/504, 125, 510/299, 329, 492

[56] References Cited

U.S. PATENT DOCUMENTS

| | | | |
|---|---|---|---|
| 3,712,873 | 1/1973 | Zenk | 260/29.2 |
| 3,915,867 | 10/1975 | Kang et al. | 252/8.8 |
| 4,370,272 | 1/1983 | Wechsler | 260/404 |
| 4,767,547 | 8/1988 | Straathof et al. | 252/8.8 |
| 5,290,475 | 3/1994 | Wixon | 252/174.23 |

FOREIGN PATENT DOCUMENTS

| | | |
|---|---|---|
| 199 403 | 10/1986 | European Pat. Off. |
| 239 910 | 10/1987 | European Pat. Off. |
| 293 955 | 12/1988 | European Pat. Off. |
| 294 894 | 12/1988 | European Pat. Off. |
| 295 739 | 12/1988 | European Pat. Off. |
| 309 052 | 3/1989 | European Pat. Off. |
| 456 569 | 11/1991 | European Pat. Off. |
| 2 409 344 | 6/1979 | France. |
| WO 91/01295 | 2/1991 | WIPO. |
| WO 92/17523 | 10/1992 | WIPO. |

OTHER PUBLICATIONS

C.R. CED Congress, Barcelona, 167 (1992), No Month.
C.R. CED Congress, Sitges, 59 (1993), No Month.
Kosmetische Färbemittel of the Farbstoffkommission der Deutschen Forschungsgemeinschaft, Verlag chemie, Weinheim, 1984, pp. 81–106, No Month.

*Primary Examiner*—Anthony Green
*Attorney, Agent, or Firm*—Ernest G. Szoke; Wayne C. Jaeschke; Real J. Grandmaison

[57] ABSTRACT

Detergent mixtures containing (a) esterquats corresponding to formulae (I), (II) or (III):

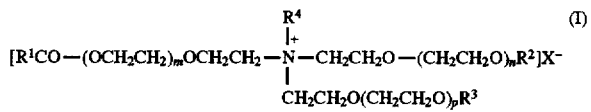

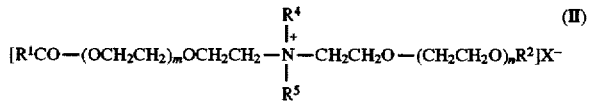

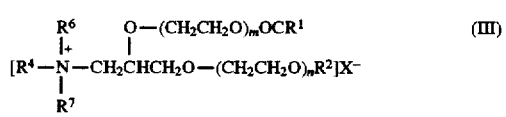

in which $R^1CO$ is an acyl radical containing 6 to 22 carbon atoms, $R^2$ and $R^3$ independently of one another represent hydrogen or have the same meaning as $R^1CO$, $R^4$, $R^5$, $R^6$ and $R^7$ independently of one another represent an alkyl group containing 1 to 4 carbon atoms or a $(CH_2CH_2O)_qH$ group, m, n and p together are 0 or numbers of 1 to 12, q is a number of 1 to 12 and X stands for halide, alkyl sulfate or alkyl phosphate, (b) soil-repelling polymers containing ethylene terephthalate or polyethylene glycol terephthalate groups, and (c) from 1% to 50% by weight of alkyl or alkenyl sulfates, based on the weight of the esterquats.

3 Claims, No Drawings

DETERGENT MIXTURES

BACKGROUND OF THE INVENTION

1. Field of the Invention

This invention relates to detergent mixtures containing esterquats and soil-repelling polymers, to formulations containing these mixtures and to the use of the mixtures for the production of surface-active formulations.

2. Discussion of Related Art

Depending on their structure, cationic surfactants have the ability to attach themselves to negatively charged surfaces, for example textile fibers or hair strands. In doing so, they reduce electrostatic charging and impart a pleasant soft feel. This effect is utilized in practice, for example in the formulation of fabric softeners or hair treatment formulations.

Whereas, until a few years ago, quaternary ammonium compounds, for example dimethyl distearyl ammonium chloride, were almost exclusively used as cationic ingredients, quaternized fatty acid triethanolamine ester salts, so-called "esterquats", which combine improved ecotoxicological compatibility with a comparable softening effect, are now being used to an increasing extent in modern fabric softeners. Reviews of this subject have been published, for example, by O. Ponsati in C.R. CED Congress, Barcelona, 167 (1992) and by R. Puchta in C.R. CED Congress, Sitges, 59 (1993).

Nevertheless, there is a market need for fabric softeners which provide fabrics with improved softness or with which the required softness can be obtained with a smaller quantity of softener.

It is also known that oily soil is very much easier to remove from hydrophilic fabrics, for example of cotton, than from hydrophobic polyester fabrics which is a result of the greater affinity of cotton for water and surfactants. This difference in behavior is explained by the chemical structure of the fibers. Polyester fibers are copolymers of terephthalic acid and ethylene glycol which contain only very few free hydroxyl or carboxyl groups onto which water can be added. By contrast, cotton consists of a cellulose material which, conversely, has a large number of hydrophilic groups. Accordingly, there is a further need on the part of the consumer for new fabric softeners which soften polyester fabrics in particular in such a way that their tendency towards soiling is reduced or oil-containing soils in particular can be readily removed in the subsequent washing process.

It would be appropriate in this connection to mention U.S. Pat. No. 3,712,873 from which the use of polyester terpolymers with a molecular weight of 1,000 to 100,000 in conjunction with quaternary ammonium compounds as fabric treatment compositions is known. The compositions are applied to the fabrics by spraying or padding and are intended to improve the soil-repelling properties of the fabrics. As comparison tests have shown, a slight improvement in the removability of oil-containing soils by washing is indeed obtained, but unfortunately softness and hydrophilicity tend to be adversely affected.

Accordingly, the problem addressed by the present invention was to provide new fabric softeners which would not be attended by any of the disadvantages mentioned above.

DESCRIPTION OF THE INVENTION

The present invention relates to detergent mixtures containing quaternary ammonium compounds (QUATS) and soil-repelling polymers containing ethylene terephthalate and/or polyethylene glycol terephthalate groups which are characterized in that they contain as QUATS quaternized fatty acid ester salts (esterquats) corresponding to formulae (I), (II) or (III):

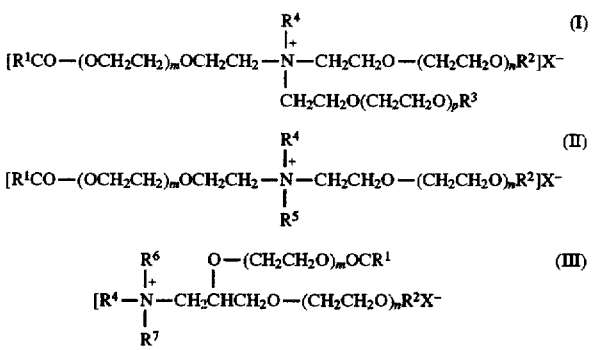

in which $R^1CO$ is an acyl radical containing 6 to 22 carbon atoms, $R^2$ and $R^3$ independently of one another represent hydrogen or have the same meaning as $R^1CO$, $R^4$, $R^5$, $R^6$ and $R^7$ independently of one another represent an alkyl group containing 1 to 4 carbon atoms or a $(CH_2CH_2O)_qH$ group, $R^5$ is an alkyl radical containing 1 to 4 carbon atoms, m, n and p together are 0 or numbers of 1 to 12, q is a number of 1 to 12 and X stands for halide, alkyl sulfate or alkyl phosphate.

It has surprisingly been found that the addition of soil-repelling polymers known per se synergistically enhances the softening effect of esterquats. The improvement in softness is accompanied by greater rewettability of the fabric. It has also been found that both textile fabrics and hair strands pretreated with the detergent mixtures according to the invention are less heavily soiled and are much easier to free from oil-containing soils than is the case where conventional softeners are used. A further synergistic improvement in these properties is achieved if anionic surfactants from the group of alkyl and/or alkenyl sulfates are added to the cationic surfactants and soil-repelling polymers.

Esterguats

Esterquats are generally understood to be quaternized fatty acid triethanolamine ester salts. They are known substances which may be obtained by the relevant methods of preparative organic chemistry. Reference is made in this connection to International patent application WO 91/01295 (Henkel), according to which triethanolamine is partly esterified with fatty acids in the presence of hypophosphorous acid, air is passed through and the reaction mixture is subsequently quaternized with dimethyl sulfate or ethylene oxide. U.S. Pat. No. 3,915,867, U.S. Pat. No. 4,370,272, EP 0 239 910 A2, EP 0 293 955 A2, EP 0 295 739 A2 and EP 0 309 052 A2 are cited at this juncture as representative of the extensive prior art.

Typical examples of esterquats corresponding to formula (I) which may be used in accordance with the invention are products based on caproic acid, caprylic acid, capric acid, lauric acid, myristic acid, palmitic acid, isostearic acid, stearic acid, oleic acid, elaidic acid, arachic acid, behenic acid and erucic acid and the technical mixtures thereof obtained, for example, in the pressure hydrolysis of natural fats and oils. Technical $C_{12/18}$ cocofatty acids and, more particularly, partly hydrogenated $C_{16/18}$ tallow fatty acid or palm oil fatty acid and also $C_{16/18}$ fatty acid cuts rich in elaidic acid are preferably used.

To produce the quaternized esters, the fatty acids and the triethanolamine may be used in a molar ratio of 1.1:1 to 3:1.

So far as the performance properties of the esterquats are concerned, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9 and are derived from technical $C_{16/18}$ tallow fatty acid or palm oil fatty acid (iodine value 0 to 40).

Quaternized fatty acid triethanolamine ester salts corresponding to formula (I), in which $R^1CO$ is an acyl radical containing 16 to 18 carbon atoms, $R^2$ has the same meaning as $R^1CO$, $R^3$ is hydrogen, $R^4$ is a methyl group, m, n and p=0 and X stands for methyl sulfate, have proved to be particularly advantageous from the performance point of view.

So far as the choice of the preferred fatty acids and the optimal degree of esterification are concerned, the examples mentioned in respect of (I) also apply to the esterquats corresponding to formulae (II) and (III). The esterquats are normally marketed in the form of 50 to 90% by weight mixtures with alcohols which, if required, may readily be diluted with water.

Soil-Repelling Polymers

The soil-repelling polymers to be used in accordance with the invention preferably contain ethylene terephthalate and/or polyethylene glycol terephthalate groups, the molar ratio of ethylene terephthalate to polyethylene glycol terephthalate being in the range from 50:50 to 90:10. The molecular weight of the linking polyethylene glycol units is preferably in the range from 750 to 5,000, i.e. the degree of ethoxylation of the polymers containing polyethylene glycol groups may be of the order of 15 to 100. The polymers are distinguished by an average molecular weight of about 5,000 to 200,000 and may have a block structure although they preferably have a random structure.

Preferred polymers are those with molar ratios of ethylene tere-phthalate to polyethylene glycol terephthalate of around 65:35 to around 90:10 and preferably in the range from about 70:30 to 80:20. Other preferred polymers are those which contain linking polyethylene glycol units with a molecular weight of 750 to 5,000 and preferably in the range from 1,000 to about 3,000 and which have a molecular weight of the polymer in the range from about 10,000 to about 50,000. Examples of commercially available polymers are the products Milease® T (ICI) or Repelotex® SRP 3 (Rhone-Poulenc).

The detergent mixtures according to the invention may contain the esterquats and the soil-repelling polymers in a ratio by weight of 70:30 to 99.5:0.5 and preferably in a ratio by weight of 75:25 to 99:1. The figures are based on the active substance content or solids content of the products.

Alkyl and/or Alkenyl Sulfates

In one preferred embodiment of the invention, the soil-repelling effect can be synergistically improved by the addition of alkyl and/or alkenyl sulfates corresponding to formula (IV):

$$R^8O—SO_3Y \qquad (IV)$$

in which $R^8$ is a linear or branched, aliphatic alkyl and/or alkenyl radical containing 6 to 22 carbon atoms and Y is an alkali metal or alkaline earth metal, ammonium, alkylammonium, alkanolammonium or glucammonium.

Typical examples of alkyl sulfates which may be used in accordance with the invention are the sulfation products of caproic alcohol, caprylic alcohol, capric alcohol, 2-ethylhexyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol and erucyl alcohol and the technical mixtures thereof obtained by the high-pressure hydrogenation of technical methyl ester fractions or aldehydes from Roelen's oxosynthesis. The sulfation products are preferably used in the form of their alkali metal salts, more especially their sodium salts. Alkyl sulfates based on $C_{16/18}$ tallow fatty alcohols or vegetable fatty alcohols of comparable C-chain distribution are particularly preferred.

The detergent mixtures according to the invention may contain the alkyl and/or alkenyl sulfates in quantities of 1 to 50% by weight and preferably in quantities of 1 to 25% by weight, based on the esterquats. These figures are again based on the active substance content or solids content.

Detergent Mixtures

The detergent mixtures according to the invention are preferably water-containing products of which the active substance or solids content may range from that of dilute solutions (2 to 10% by weight) to concentrates (10 to 20% by weight) and multiple concentrates (20 to 40% by weight). To produce the detergent mixtures, either dilute solutions or concentrates of the individual substances are mixed by stirring, optionally at elevated temperature, the sequence in which the components are mixed not being critical. Their mixing is a purely mechanical process which does not involve a chemical reaction. If concentrates are produced, they may be marketed and diluted to the in-use concentration in situ by the user. The water-containing detergent mixtures may also be conventionally spray-dried in known manner or treated with superheated steam. The water-free products obtained are distinguished by particularly favorable solubility or dispersibility in cold water.

Commercial Applications

The detergent mixtures according to the invention provide textiles, fibers and woven fabrics and also hair strands with a pleasant softness, improve their rewettability and reduce antistatic charging. Textiles, fibers, woven fabrics and hair pretreated with the detergent mixtures according to the invention soil to a lesser extent and, in addition, are easier to free from oil-containing soils.

Accordingly, the present invention relates to water-based textile or fiber auxiliaries containing a) 2 to 40% by weight and preferably 2 to 10% by weight of esterquats, b) 0.01 to 5% by weight and preferably 0.1 to 5% by weight of soil-repelling polymers and optionally c) 0.1 to 10% by weight of alkyl and/or alkenyl sulfates.

The present invention also relates to water-based hair treatment formulations containing a) 0.5 to 10% by weight of esterquats, b) 0.01 to 5% by weight of soil-repelling polymers and optionally c) 0.1 to 10% by weight of alkyl and/or alkenyl sulfates.

Finally, the present invention relates to the use of the detergent mixtures according to the invention for the production of surface-active formulations, more especially textile or fiber auxiliaries, for example conditioners and softeners and hair treatment formulations, for example shampoos and rinses, in which the mixtures may be present in quantities of 1 to 50% by weight and preferably 3 to 25% by weight, based on the formulation.

Auxiliaries and Additives

The detergent mixtures according to the invention may contain other auxiliaries and additives of which the type and quantity are determined by the particular application envisaged. Thus, the mixtures may contain small quantities of other surfactants compatible with the other ingredients. Typical examples are fatty alcohol polyglycol ether sulfates, ether carboxylic acids, monoglyceride sulfates, alkyl amidobetaines or protein fatty acid condensates.

Other auxiliaries and additives which the detergents mixtures according to the invention may contain are emulsifiers, such as alkoxylated fatty alcohols or sorbitan esters. Superfatting agents may be selected from such substances as, for example, polyethoxylated lanolin derivatives, lecithin derivatives and fatty acid alkanolamides, the fatty acid alkanolamides also serving as foam stabilizers. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone and electrolytes, such as sodium chloride and ammonium chloride. In the context of the invention, biogenic agents are, for example, plant extracts, protein hydrolyzates and vitamin complexes. Conventional film formers are, for example, polyvinyl pyrrolidone, vinyl pyrrolidone/vinyl acetate copolymers, polymers of the acrylic acid series, quaternary cellulose derivatives and similar compounds. Suitable preservatives are, for example, phenoxyethanol, formaldehyde solution, parabens, pentadiol or sorbic acid. Suitable pearlescers are, for example, glycol distearic acid esters, such as ethylene glycol distearate, and also fatty acid monoglycol esters. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are normally used in concentrations of 0.001 to 0.1% by weight, based on the mixture as a whole.

In all, the auxiliaries and additives may make up 1 to 50 and preferably 5 to 40% by weight of the formulations.

The following Examples are intended to illustrate the invention without limiting it in any way.

EXAMPLES

I. Ingredients Used

A1) Methyl-quaternized ditallow fatty acid triethanolamine ester in the form of the methyl sulfate salt Dehyquart® AU 46, Pulcra S. A., Barcelona, Spain A2) Dimethyl distearyl ammonium chloride Präpagen® W. K., Hoechst AG, Frankfurt, FRG A3) 1-Methyl-2-tallow-3-tallow fatty aminoamidoethyl imidazolinium methosulfate Rewoquat® W 7500, Rewo Chemische Werke GmbH, Steinau a.d.Str, FRG B1) Terephthalic acid/ethylene glycol/polyethylene glycol/ polyester/sodium sulfate mixture (1:1) Repelotex® SRP 3, Rhone-Poulenc C1) Tallow fatty acid sulfate sodium salt Sulfopon® T55, Henkel KGaA, Düjsseldorf, FRG II. Performance Tests a) Softening Effect. Cotton cloth (molleton) hardened by repeated washing was treated with formulations F1 to F11 in a Wacker machine.

The following parameters were adjusted:

| Concentration | 4 g/l |
| Liquor load | 1 part fabric: 10 parts water |
| Water hardness | 16°d |
| Rinsing time | 5 mins. |

Softness was subjectively evaluated by 6 experienced examiners who awarded scores on a scale of 0 to 6 (0=hard and rough, 6=soft and full).

B) Soil Repelling Power. In a launderometer, a polyester (crease-resistant) fabric was treated with softener formulations F1 to F11 over 5 cycles. The following parameters were adjusted:

| Softener dosage | 4 g/l |
| Liquor load | 1 part fabric: 10 parts water |
| Water hardness | 16°d |
| Rinsing time | 10 mins. |

After each of the 5 cycles, the fabrics were washed at 40° C. with a phosphate-free universal detergent (Dixan®, Henkel KGaA, dosage 10 g/l, liquor 1:10). 1 ml of soiled engine oil was then applied to the fabrics. The soiled fabrics pretreated with the softener formulations were then rewashed and visually evaluated for stain removal on the following scale:

| 0 = complete stain removal |
| 1 = traces visible |
| 2 = slight stain residues |
| 3 = distinctly visible stain residues |
| 4 = large stain residues |
| 5 = stain fully intact |

The results are set out in Table 1. Formulations F1 to F5 correspond to the invention while formulations F6 to F11 are intended for comparison. The percentages are % by weight.

TABLE 1

Softening Effect and Soil-Repelling Effect

| Ex. | F | A1 % | A2 % | A3 % | B1 % | C1 % | SE | SRE |
|---|---|---|---|---|---|---|---|---|
| 1 | F1 | 4.5 | — | — | 0.5 | — | 5.5 | 0.5 |
| 2 | F2 | 4.0 | — | — | 1.0 | — | 4.8 | 0.5 |
| 3 | F3 | 3.8 | — | — | 1.2 | — | 4.5 | 0.5 |
| 4 | F4 | 4.0 | — | — | 0.5 | 0.5 | 4.5 | 0.5 |
| 5 | F5 | 3.5 | — | — | 0.5 | 1.0 | 4.0 | 0 |
| CE1 | F6 | — | 4.5 | — | 0.5 | — | 4.5 | 1.0 |
| CE2 | F7 | — | — | 4.5 | 0.5 | — | 4.5 | 1.0 |
| CE3 | F8 | 5.0 | — | — | — | — | 5.0 | 3.5 |
| CE4 | F9 | — | 5.0 | — | — | — | 5.0 | 3.5 |
| CE5 | F10 | — | — | 5.0 | — | — | 5.0 | 3.5 |
| CE6 | F11 | — | — | — | 0.5 | — | 1.0 | 1.0 |

Legend:
F = Formulation
SE = Softening effect
SRE = Soil repelling effect

The Examples show that combinations of esterquats with the soil-repelling polymers lead to better softness and better stain removal than combinations of conventional QUATS with the same soil-repelling polymers. The stain-removing effect can be further improved by addition of alkyl sulfates.

We claim:

1. Detergent mixtures comprising (a) esterquats corresponding to formulae (I), (II) or (III):

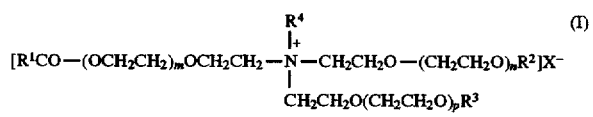

-continued

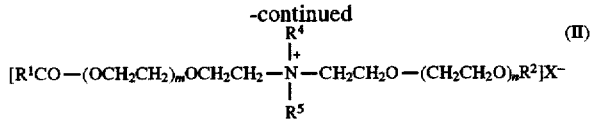

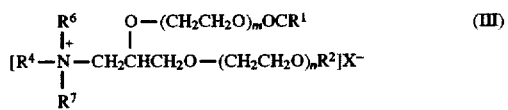

in which $R^1CO$ is an acyl radical containing 6 to 22 carbon atoms, $R^2$ and $R^3$ independently of one another represent hydrogen or have the same meaning as $R^1CO$, $R^4$, $R^5$, $R^6$ and $R^7$ independently of one another represent an alkyl group containing 1 to 4 carbon atoms or a $(CH_2CH_2O)_qH$ group, m, n and p together are 0 or numbers of 1 to 12, q is a number of 1 to 12 and X stands for halide, alkyl sulfate or alkyl phosphate, (b) soil-repelling polymers containing ethylene terephthalate or polyethylene glycol terephthalate groups, wherein said esterquats and said soil-repelling polymers are present in a ratio by weight of 70:30 to 99.5:0.5, and (c) from 1% to 50% by weight of alkyl or alkenyl sulfates, based on the weight of said esterquats.

2. Detergent mixtures as in claim 1 wherein said esterquats and said soil-repelling polymers are present in a ratio by weight of 75:25 to 99:1.

3. Detergent mixtures as in claim 1 wherein said alkyl or alkenyl sulfates correspond to formula (IV):

in which $R^8$ is a linear or branched, aliphatic alkyl or alkenyl radical containing 6 to 22 carbon atoms and Y is an alkali metal or alkaline earth metal, ammonium, alkylammonium, alkanolammonium or glucammonium.

* * * * *